United States Patent
Krill et al.

(10) Patent No.: US 9,816,703 B2
(45) Date of Patent: *Nov. 14, 2017

(54) RECIRCULATION AND DISPOSAL OF AQUEOUS CATALYST SOLUTIONS IN AMINE CATALYTIC PROCESSES

(71) Applicant: EVONIK ROEHM GmbH, Darmstadt (DE)

(72) Inventors: Steffen Krill, Muehltal (DE); Torsten Balduf, Pfungstadt (DE); Rudolf Burghardt, Darmstadt (DE); Gerhard Koelbl, Gernsheim (DE); Reed Zhao, Shanghai (CN)

(73) Assignee: EVONIK ROEHM GmbH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/904,898

(22) PCT Filed: Jul. 15, 2014

(86) PCT No.: PCT/EP2014/065067
§ 371 (c)(1),
(2) Date: Jan. 13, 2016

(87) PCT Pub. No.: WO2015/010944
PCT Pub. Date: Jan. 29, 2015

(65) Prior Publication Data
US 2016/0138804 A1    May 19, 2016

(30) Foreign Application Priority Data

Jul. 24, 2013 (EP) ..................... 13177840

(51) Int. Cl.
*F23G 7/00* (2006.01)
*C07C 45/75* (2006.01)
(Continued)

(52) U.S. Cl.
CPC .............. *F23G 7/008* (2013.01); *C07C 45/75* (2013.01); *C07C 45/82* (2013.01); *F23G 5/14* (2013.01); *F23G 7/001* (2013.01); *F23G 7/065* (2013.01)

(58) Field of Classification Search
CPC . F23G 5/14; F23G 7/001; F23G 7/008; F23G 7/065; C07C 47/22; C07C 45/75; C07C 45/82
(Continued)

(56) References Cited

U.S. PATENT DOCUMENTS

| 4,316,878 A | 2/1982 | Akune et al. |
| 4,496,770 A | 1/1985 | Duembgen et al. |

(Continued)

FOREIGN PATENT DOCUMENTS

| DE | 30 04 186 | 8/1980 |
| DE | 32 13 681 A1 | 10/1983 |

OTHER PUBLICATIONS

Fang ("Reverse Osmosis Separation of Polar Organic Compounds in Aqueous Solution" Environmental Science and Technology, vol. 10, No. 4, 1976, p. 364-369).*

(Continued)

*Primary Examiner* — Jafar Parsa
*Assistant Examiner* — Amy C Bonaparte
(74) *Attorney, Agent, or Firm* — Oblon, McClelland, Maier & Neustadt, L.L.P.

(57) ABSTRACT

The present invention relates to the oxidative combustion of amine-containing wastewaters, especially in a process for preparing methacrolein. Methacrolein is used in chemical synthesis particularly as an intermediate for preparation of methacrylic acid, methyl methacrylate, or else of active ingredients, odorants or flavorings. More particularly, the present invention relates to an oxidative combustion of the (Continued)

amine-containing wastewaters with only low nitrogen oxide formation.

16 Claims, 1 Drawing Sheet

(51) Int. Cl.
    *C07C 45/82*     (2006.01)
    *F23G 5/14*     (2006.01)
    *F23G 7/06*     (2006.01)

(58) Field of Classification Search
    USPC .................................. 110/238; 562/598, 600
    See application file for complete search history.

(56) References Cited

U.S. PATENT DOCUMENTS

| 2016/0031786 A1 | 2/2016 | Balduf et al. |
| 2016/0068464 A1 | 3/2016 | Krill et al. |
| 2016/0159719 A1* | 6/2016 | Burghardt ............. C07C 45/786 568/461 |

OTHER PUBLICATIONS

Bauer ("Methacrylic Acid and Derivatives" Ullmann's Encyclopedia of Industrial Chemistry, p. 1-12, pub. online Oct. 15, 2011, DOI: 10.1002/14356007.a16_441.pub2).*
Reuss ("Formaldehyde", Ullmann's Encyclopedia of Industrial Chemistry, p. 735-768, published online Jun. 15, 2000, DOI: 10.1002/14356007.a11_619).*
International Search Report dated Sep. 24, 2014 in PCT/EP14/65067 Filed Jul. 15, 2014.
European Search Report dated Nov. 20, 2013 in EP 13177840.9 Filed Jul. 24, 2013.
U.S. Appl. No. 14/916,440, filed Mar. 3, 2016, Krill, et al.
U.S. Appl. No. 14/904,777, filed Jan. 13, 2016, Burghardt, et al.
U.S. Appl. No. 15/037,171, filed May 17, 2016, Burghardt, et al.
U.S. Appl. No. 15/030,775, filed Apr. 20, 2016, Krill, et al.

* cited by examiner

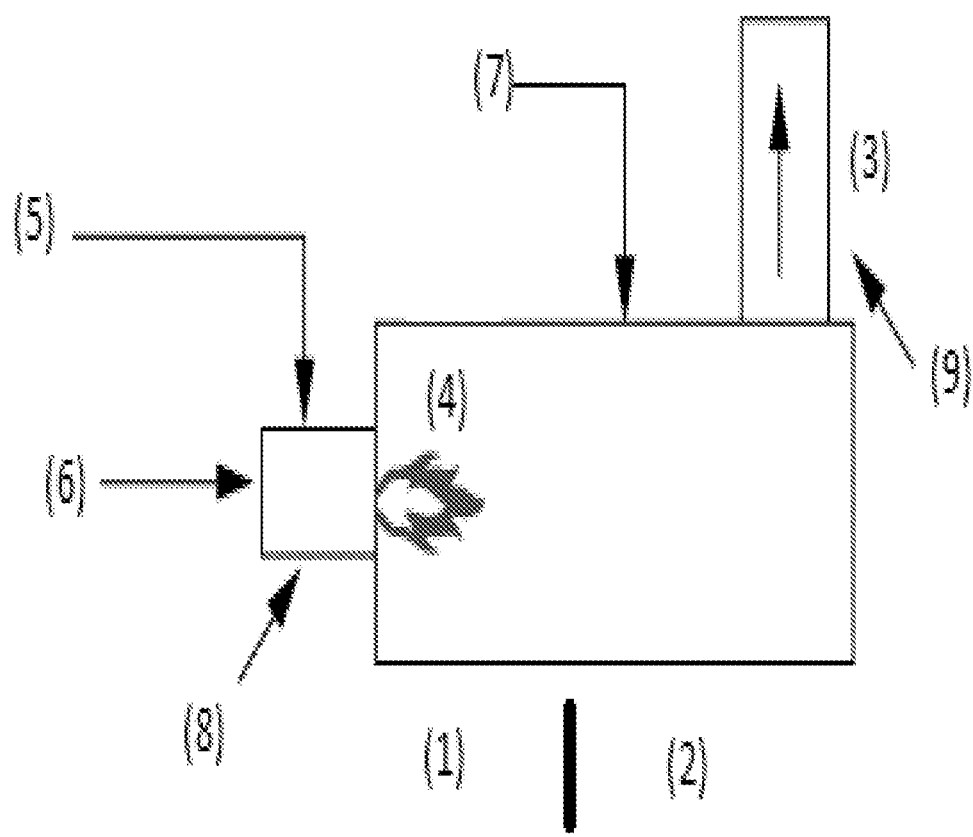

RECIRCULATION AND DISPOSAL OF AQUEOUS CATALYST SOLUTIONS IN AMINE CATALYTIC PROCESSES

The present invention relates to the oxidative combustion of amine-containing wastewaters, especially in a process for preparing methacrolein.

Methacrolein is used in chemical synthesis particularly as an intermediate for preparation of methacrylic acid, methyl methacrylate, or else of active ingredients, odourants or flavourings. More particularly, the present invention relates to an oxidative combustion of the amine-containing wastewaters with only low nitrogen oxide formation.

There is a great interest in very simple, economically viable and environmentally friendly preparation processes for methacrolein.

STATE OF THE ART

There are various amine-catalytic processes in which amine-containing water of reaction is obtained. One example of these is the industrial scale process for preparation of methacrolein, proceeding from propanal and formaldehyde. The reaction is effected by means of a Mannich reaction. A process of this kind for preparation of methacrolein is described in publications including U.S. Pat. No. 7,141,702, U.S. Pat. No. 4,408,079, JP 3069420, JP 4173757, EP 0 317 909 and U.S. Pat. No. 2,848,499.

There is of course a particular interest in this context in conducting this reaction continuously. At the same time, amine-containing water is obtained as a by-product of the Mannich reaction or of an aldol-like addition. This water is firstly the reaction medium and solvent for reactants and catalyst solution, and is required especially for moderation of the heat of reaction and of the running of the reaction. On the other hand, in such a process, the water, for example comprising the catalyst, is recycled. A disadvantage of this procedure is, however, that the water accumulates in the reaction circuit with time and has to be removed. After substantial removal from the reaction product, the methacrolein, the water together with active and inactive catalyst constituents is sent to a thermal oxidizer for disposal in the form of oxidative combustion. It should additionally be taken into account that considerable amounts of water also get into the system with the formalin starting material, according to the chosen strength or concentration of the formalin (typically, formalin concentrations customary in the trade and in production of between 36-60 wt % of formaldehyde in water are used), thus resulting per se in a baseload of water which has to be treated together with the water formed during the reaction after removal from the methacrolein product of value. Furthermore, with regard to the water budget in the reaction and workup, it has to be taken into account that the side reactions also release water. This applies both to the side reactions of the propanal and to the by-products of the catalytically active amines. The catalytically active amines form, under the reaction conditions according to Eschweiler-Clarke or in a Leuckart-Wallach-like reaction, more highly alkylated derivatives, some of which are no longer catalytically active. By way of example, the reaction of dimethylamine with one formaldehyde equivalent forms trimethylamine, while water is released.

DE 32 13 681 suggests several alternatives in this regard. In the case of small amounts of catalyst in the aqueous phase, or the distillation bottoms, which, as well as the aqueous phase and the catalyst, additionally comprises high-boiling by-products and residual reactants and methacrolein, the suggestion is to dispose thereof. In the case of higher concentrations, the suggestion is to subject the bottoms to a further, very complex distillation in order to reduce the amount of water. In this case, the rest is then conducted back into the reaction space. This procedure, however, is not just energetically unfavourable but also reduces the yield by discarding methacrolein in such a further distillation, this being distilled off as well because of the relatively low boiling point.

In a third alternative of DE 32 13 681, the bottoms are divided and a portion is recycled into the reaction space such that the water content therein remains constant. The other portion of the bottoms—and hence the aqueous phase—is discarded. DE 32 13 681 does not disclose whether and how this aqueous solution has worked up.

If the water is not distilled off, it generally cannot be sent to any biological utilization because of relatively high contamination with catalyst, reactants, product and by-products. Instead, the wastewater has to be subjected to oxidative combustion. Because of the high amine content, for example in the wastewater of a Mannich reaction or of an aldol condensation, such combustion according to the prior art gives rise to large amounts of nitrogen oxides. These subsequently have to be catalytically broken down or removed before the combustion gases can be emitted. Such a procedure is associated with corresponding capital costs.

A simple known alternative is that of feeding ammonia into the thermal oxidizer. A thermal oxidizer of this kind can be roughly divided into three regions. In the first region is the burner. At this point, the liquid to be combusted, in this case an amine-containing aqueous solution, and air are fed in. In the second region downstream, oxidative combustion is effected. In this zone, nitrogen oxides are formed from amines. In a third zone, at the end of the thermal oxidizer, the oxygen content is so low that the combustion is reductive if anything. It is accordingly also possible to refer to the second stage as the oxidative zone and to the third region as the reductive zone of the thermal oxidizer. In the reductive zone, the oxygen content is generally below 2.5% by volume.

It is known from the prior art that the nitrogen oxide contents can be reduced prior to the ultimate emission by feeding of ammonia into the reductive zone. The disadvantage of this procedure, however, is that a further feed line is needed as well as the air feed, and an equimolar amount of ammonia has to be used to reduce nitrogen oxide formation or to reduce nitrogen oxides formed again, in order to meet the national standards for licensing purposes.

There is thus an urgent need for an effective and simultaneously environmentally friendly method for combustion of amine-containing waters of reaction in the preparation of methacrolein by the process elucidated above.

Problem

In view of the prior art, the problem addressed by the present invention was therefore that of disposing of the amine-containing wastewater obtained in an amine-catalytic reaction with avoidance of the formation of nitrogen oxides above a waste air concentration of 500 ppm, especially of 250 ppm.

In view of the prior art, it was a particular problem to provide a method with which it is possible to dispose of the amine-containing wastewater with avoidance of the formation of nitrogen oxides over and above the existing baseload of a thermal oxidizer.

An additional problem addressed by the present invention was that of using a minimum amount of ammonia in the process.

A particular problem addressed by the present invention was that of disposing of the amine-containing water of reaction from a continuously operated Mannich reaction for preparation of methacrolein in an environmentally friendly manner.

Moreover, the method was to be implementable by relatively simple and inexpensive modifications to existing plants. The modifications were accordingly to be associated with a low level of capital costs. At the same time, the plants even after the modification were to be simple to maintain and cause low maintenance costs.

Further objects which are not specified explicitly are apparent from the overall context of the description which follows and of the claims.

BRIEF DESCRIPTION OF THE SEVERAL VIEWS OF THE DRAWINGS

FIG. 1: Thermal oxidizer operated in accordance with the invention.

Solution

These problems are solved by a novel method for oxidative combustion of amine-containing water of reaction. In this method, the amine-containing water of reaction is combusted in a thermal oxidizer. A thermal oxidizer of this kind generally consists of a first zone having the burner, the fuel feed and the air feed, a second, oxidative zone, and a third, reductive zone having an oxygen content less than 3% by volume.

The method can thus be effected, for example, by a slight modification to known thermal oxidizers. This is effected in the form of an addition of a feed line to the first zone, to the second, oxidative zone or to the third, reductive zone of the thermal oxidizer.

The thermal oxidizers used in accordance with the invention generally have at least three zones. The first is the burner, comprising a combustion chamber. In many plants, this combustion chamber is spatially divided from the further, second zone, with a connection line, such that the differentiation of the two zones is readily apparent to the person skilled in the art. In embodiments in which the two zones merge seamlessly into one another, the boundary to the second zone is considered to be where the temperature is below 1100° C. In the flame itself, the temperature is not usually below this level. The first zone, also called combustion chamber or burner, comprises, as well as the burner, which is usually operated with natural gas, additionally an air feed and optionally an inlet for liquid fuels. These liquid fuels may be organic compounds, for example heavy oil or solvents, or organic, readily combustible wastes from a plant. The liquid fuels are required firstly for additional firing, and it is secondly possible here to combust organic, non-amine-containing by-products from another production operation and hence dispose of them in an environmentally compliant manner. The air supplied can be heated before being fed in, in order thus to enable more efficient combustion in this region. Additionally optionally, in the first zone, it is also possible to feed in waste air streams from production processes, especially those comprising organic constituents, for additional combustion and/or increase in the combustion power.

In an optional embodiment, the amine-containing water of reaction is fed into this first zone, in this case preferably directly into the flame of the burner.

In a second, preferred embodiment of the method according to the invention, the amine-containing water of reaction is fed into the second, oxidative zone. The second, oxidative zone, often referred to as the combustion chamber, is notable for a lower temperature compared to the first zone, with a simultaneously high oxygen content. In general, the oxygen content in the front region of the second zone is higher than in the rest of the region. The second zone may be set up either horizontally or vertically. The first zone is preferably set up vertically. Preferably, the amine-containing aqueous solution is fed in by means of a two-phase nozzle. Such a two-phase nozzle achieves optimal atomization and hence conversion of the organic and amine-containing fractions of the water of reaction injected. As well as the water of reaction, air, steam or another carrier gas, preferably air, is injected via the two-phase nozzle for better distribution. Two-phase nozzles can also be used in the other optional embodiments.

This oxidative zone of the thermal oxidizer preferably has a temperature between 850 and 1100° C., more preferably between 880 and 1080° C. and most preferably between 900 and 950° C. The oxygen content, viewed over the whole second, oxidative zone, is preferably between 3 and 21% by volume, especially between 5 and 21% by volume, where a gradient may be present within the oxidative zone. As a result of the oxidative processes, oxygen is consumed in the direction of the transition to the reductive zone. Accordingly, the oxygen content in the region of the feed or injection point of the amine-containing water of reaction is preferably between 10 and 21% by volume, more preferably between 15 and 21% by volume.

In a third, optional embodiment of the invention, the amine-containing water of reaction is injected into a third zone of the thermal oxidizer, in which a reductive conversion is effected. This zone too is usually divided spatially from the second zone, with a passage through. For plants in which there is no such divide, the transition can be determined by the person skilled in the art via the oxygen content. It is a feature of the reductive zone that the oxygen content is below 3% by volume. The temperature within this third zone is usually similar to the temperature in the second zone and is generally between 850 and 1000° C., especially between 900 and 950° C. In this zone—irrespective of the particular embodiment—the optional injection of denitrification reagents, for example aqueous ammonia solution, for reduction of the nitrogen oxides can also be effected.

According to the invention, oxygen content means the content of elemental oxygen. Oxygen chemically bonded to other elements, for example $CO_2$ or CO, is not counted as part of the oxygen content.

Following this third zone, thermal oxidizers usable in accordance with the invention may have further constituents. These further constituents include, for example, a delay zone which is preferably present, in which kinetically slow reductive processes can proceed further. This may be followed, for example, by one or more heat exchangers. By means of these, it is possible, for example, to generate steam for the production plants, for the two-phase nozzles, for heating of the air fed into the combustion chamber, or for heating of the wastewater streams to be combusted. In this way, an energetically efficient mode of operation in relation to the fuel used in the thermal oxidizer can be implemented. Finally, the thermal oxidizer has a downcomer or similar.

The method of the invention is used for workup of amine-containing water of reaction from a Mannich reaction—preferably conducted continuously—in which propanal is reacted with formaldehyde to give methacrolein. As alternative to the direct addition of formaldehyde, this may especially also be a process with addition of formalin or paraformaldehyde, which are explicitly also encompassed hereinafter by the term formaldehyde.

The processes which are based on a Mannich reaction and are suitable for preparation of methacrolein are known to those skilled in the art and are the subject of relevant review articles, for example in Ullmann's Encyclopedia of Industrial Chemistry 2012, Wiley-VCH Verlag GmbH & Co. KGaA, Weinheim, Acrolein and Methacrolein, DOI: 10.1002/14356007.a01_149.pub2. More particularly, the method conducted with particular preference in accordance with the invention prior to the feeding-in of the amine-containing water of reaction relates to a continuously conducted Mannich reaction as disclosed in European patent application 13002076.1. According to the invention, such a preferred preliminary stage is illustrated by reference to the disclosure-content of this application relating to the methacrolein synthesis.

A particularly preferred Mannich reaction of this kind is performed in the presence of 0.1 to 20 mol % of organic base, preferably a secondary amine, and 0.1 to 20 mol % of acid, based in each case on the propanal used, at a temperature of 100 to 300° C. and at a pressure of 5 to 100 bar.

The acids are generally inorganic acids or organic mono-, di-or polycarboxylic acids, preferably monocarboxylic acids, especially aliphatic monocarboxylic acids. Particular preference is given to converting propanal and formaldehyde using at least one organic acid, more preferably acetic acid. The proportion of acid is between 0.1 and 20 mol %, advantageously from 0.5 to 10 mol %, preferably 1 to 5 mol %, based on propanal.

The organic bases are preferably amines, more preferably secondary amines. Examples of useful amines include: dimethylamine, diethylamine, methylethylamine, methylpropylamine, dipropylamine, dibutylamine, diisopropylamine, diisobutylamine, methylisopropylamine, methylisobutylamine, methyl-sec-butylamine, methyl(2-methylpentyl)amine, methyl(2-ethylhexyl)amine, pyrrolidine, piperidine, morpholine, n-methylpiperazine, n-hydroxyethylpiperazine, piperazine, hexamethyleneimine, diethanolamine, methylethanolamine, methylcyclohexylamine, methylcyclopentylamine, dicyclohexylamine or corresponding mixtures. The proportion of organic base is between 0.1 and 20 mol %, advantageously from 0.5 to 10 mol %, preferably 1 to 5 mol %, based on propanal.

The ratio of equivalents of amine to acid is preferably selected so as to result in a pH of 2.5 to 9 in the reaction mixture prior to the reaction.

In the amine-containing water of reaction which is to be disposed of in accordance with the invention, as well as the components and by-products mentioned, additionally remaining reactants or conversion products thereof may be present. More particularly, these are the catalyst components, such as a secondary amine and an organic acid, and the salt formed therefrom. By-products of these catalysts are of particular interest with regard to disposal. Examples here include, in particular, more highly alkylated amines, such as trimethylamine in particular when dimethylamine was used as the original catalyst amine. It is also possible for small amounts of reactant or product to be present in the amine-containing water of reaction. Examples of these are methacrolein, formaldehyde, paraformaldehyde and propanal.

By-products of the reaction likewise present in the amine-containing water of reaction would be, for example, dimers, oligomers or polymers of methacrolein. In addition, according to the process regime, it is also possible for further auxiliaries, such as organic solvents, for example methanol, formic acid, propanol, dioxane, tetrahydrofuran or methoxyethanol to be present, and also further substances present or formed in the reaction matrix.

In such a process, the product, i.e. the methacrolein, is generally removed by means of a distillation column. The reaction solution to be worked up can be fed onto the column, into the column or beneath the column. In the vaporizer section of this column, a bottoms composition collects, consisting predominantly of the water of reaction, or comprising the amounts of water which get into the circulation process with the formalin solution. This additionally comprises the catalyst components, for example the organic acid and the secondary amine or the salt formed therefrom, and also by-products of the reaction, from the catalyst solution or from the combination of the two. Such a by-product from the catalyst solution may, for example, be trimethylamine, which has formed from dimethylamine. This aqueous catalyst solution can preferably be drawn off below the feed, especially at the bottom of the column. The water of reaction produced in this way is composed of the water which has been added as catalyst solution, the water formed in the reaction and optionally the water from the formaldehyde solution. Further water sources which should be taken into account but to a lesser degree are constituents of the technical-grade reactants such as propanal, and water which is formed in various side reactions of the catalyst components with reactants, by-products and reaction products, and water of reaction from all these components which form under the reaction conditions.

In an alternative process configuration, the amine-containing water of reaction is separated from the product by means of a phase separator, and the amine-containing water of reaction from this phase separator is fed, directly or after further workup, fully or partly to the thermal oxidizer. The organic phase in turn is then sent to a distillation column, by means of which the methacrolein is recovered. The bottoms from this distillation column in turn can be conducted back into the phase separator, into the reaction space, or likewise fully or partly into the thermal oxidizer.

For the further processing, if very little amine and/or acid is used and it is therefore not worth recycling the catalyst, the bottoms liquid can be discarded. Because of the nevertheless high level of organic contamination, especially with amines, such water is not amenable to direct biological workup and has to be disposed of thermally, more particularly by means of a thermal oxidizer.

In the case of relatively high amine and/or acid concentrations in the bottoms output, however, the water can also be partly removed by distillation and the catalyst solution can be recycled back into the reactor. In such a process, however, by-products accumulate in this catalyst solution, and so it has to be regularly renewed, and the discharged portion has to be disposed of thermally, analogously to processes described above.

It is also possible to divide the bottoms output into two substreams, such that one substream carries the exact amount of water which is formed in the reaction or has been introduced with the starting materials. This substream is then discharged and the remaining fraction is recycled into the reactor. The discharged portion would be disposed of thermally in this method.

More preferably in accordance with the invention, the amine-containing water of reaction is withdrawn partly below the feed, preferably from the bottom of a distillation column, and disposed of thermally by means of a thermal oxidizer described. The rest of the bottoms is passed into the reaction space of the plant.

Preferably, the amine-containing water of reaction, based on the natural gas rate to the burner, is metered into the oxidative zone in an amount between 0.3 and 3.6 mol/m$^3$ (STP). It is additionally preferable that the amine metered in, based on the total amount of water metered into the thermal oxidizer, is present in a concentration between 17 and 350 mol/m$^3$.

In a further embodiment of the present invention, the amine-containing water of reaction withdrawn, for example, from the bottom of the distillation column is passed through a membrane separation stage. The retentate obtained, i.e. the lower-water phase relative to feed stream prior to the membrane stage, can then either be recycled partially or completely into the reaction circuit or discharged and sent to the thermal oxidizer in accordance with the invention. Alternatively or additionally, the permeate, in the case that the organic or aminic constituents are at too high a level for another kind of utilization or disposal, can also be sent to the thermal oxidizer in accordance with the invention. In this way, optimal control of water content and catalyst content in the reaction space is possible, with simultaneous optimal exploitation and reduction of the amount of catalyst needed for a required conversion, and the safe and environmentally compliant disposal of the aqueous catalyst solution remaining, with the ability to control and reduce the nitrogen oxide emissions produced in the thermal oxidizer and with simultaneous generation of a higher calorific value in this phase supplied to the thermal oxidizer than that which is generated originally by a single path of the reaction. This allows saving of natural gas, or fuel in general.

In one variant of the method according to the invention, ammonia, urea or an amine is additionally metered into the reductive zone of the thermal oxidizer. In relation to this additional, optional feature, this variant corresponds to the prior art and serves to further reduce the proportion of nitrogen oxides formed. The reduction forms mainly elemental nitrogen. By virtue of the method according to the invention, however, it is necessary to feed only distinctly reduced amounts of one of the substances listed into the reductive zone as compared with the prior art. Preferably, the method, however, is conducted entirely without this additional feed.

In a further variant of the present method according to the invention, a liquid to be combusted, comprising organic constituents, from another process is additionally metered into the first or second zone of the thermal oxidizer. This liquid may likewise be purely organic or may take the form of an aqueous solution or mixture. The metered addition can usually be effected directly into the flame in the first zone, separately in the second zone, or together with the amine-containing water of reaction.

More preferably, the liquid additionally metered in in this variant comprises waste products from the conversion of methacrolein to methyl methacrylate and/or the conversion of methacrolein directly to methacrylic acid. Corresponding processes are described and discussed in detail in Nagai et al., (http://www.sumitomo-chem.co.jp/english/rd/report/theses/docs/20040200_30a.pdf). More particularly, these include the direct oxidative esterification of methacrolein to MMA and the gas phase oxidation of methacrolein to methacrylic acid.

In a further variant of the present method according to the invention, a liquid to be combusted or gas streams to be combusted, comprising organic constituents, from further processes is/are additionally fed into the first or second zone of the thermal oxidizer, especially those further processes which provide the reactants for the methacrolein process according to the invention. Particular mention should be made here of processes for production of the starting materials for the methacrolein process, such as the propanal process proceeding from ethylene and synthesis gas, and various formalin processes proceeding from methanol. These liquids may likewise be present purely in organic form or as an aqueous solution or mixture. The metered addition can usually be effected directly into the flame in the first zone, separately in the second zone, or together with the amine-containing water of reaction. More preferably, the liquid metered in additionally in this variant comprises waste products from the reaction of ethylene and synthesis gas to give propanal and/or the conversion of methanol to formalin.

Processes for preparing propanal have likewise been described extensively in the literature, as has the generation of pentenal-containing organic wastes which arise from side reactions of the hydroformylation of ethylene through consecutive reaction of the desired product and which can also be combusted and utilized thermally by the method according to the invention together with the amine-containing phase of the methacrolein process.

It is a great advantage of the method according to the invention that it can be performed with relatively simple and inexpensive plants. The plants are associated with a low level of capital costs. At the same time, the plants are easy to maintain and cause a low level of maintenance costs.

The examples which follow serve to further elucidate preferred embodiments of the present invention, without any intention that this should impose a restriction of the invention.

EXAMPLES

A thermal oxidizer, designed for combustion of 35 tons of wastewater per hour, was used. In doing so, it produces 73 tons of steam (36 bar at 343° C.) per hour. In this process, 4.5 tons of natural gas per hour are burnt, which corresponds to a power consumption of about 62 MW. The thermal oxidizer is additionally equipped with an inlet into the oxidation zone of the thermal oxidizer. This inlet has an air-operated two-phase nozzle. The water of reaction used was a wastewater comprising 40% by weight of dimethylamine. The nitrogen oxide concentrations reported were measured inline by means of IR analysis in the offgas and relate to a stable state which is attained after a few minutes of operation. The following process parameters were observed in all experiments:

Flow rate of the wastewater: 21.6 to 23.5 tons/hr
Gas phase temperature in reductive zone: 870 to 905° C.
Offgas rate: 128000 to 132000 m$^3$/h
Waste air feed (additional process air with low organic content): 2000 m$^3$ (STP)/h
Concentration of the ammonia solution: 20% by weight In Inventive Examples 1 to 7, the amine-containing waters of reaction were fed into the oxidative zone of the thermal oxidizer. In Examples 1 to 6, an ammonia solution was additionally sprayed into the reductive zone of the thermal oxidizer. This was not done in Example 7.

In Baseload Examples 1 to 4 the dimethylamine solution was not fed in, and in Baseload Example 1 the ammonia was additionally not fed in either. The value for the nitrogen oxide concentration in the offgas measured in Baseload Example 1 can be viewed as the baseload of the thermal oxidizer. These nitrogen oxides form from the elemental nitrogen in the air fed in, usually within the flame itself.

In the likewise Inventive Examples 8 to 10, the dimethylamine solution was fed directly into the first zone of the thermal oxidizer (the combustion chamber).

|  | Dimethylamine solution kg/h | Ammonia solution kg/h | NOx in the offgas mg/m³ |
|---|---|---|---|
| Example 1 | 220 | 180 | 35 |
| Example 2 | 400 | 180 | 35 |
| Example 3 | 500-550 | 180 | 38 |
| Example 4 | 600 | 150 | 37 |
| Example 5 | 625 | 100 | 37 |
| Example 6 | 650 | 50 | 40 |
| Example 7 | 650-700 | 0 | 45-50 |
| Baseload Example 1 | 0 | 0 | 90-100 |
| Baseload Example 2 | 0 | 35 | 55 |
| Baseload Example 3 | 0 | 70 | 30 |
| Baseload Example 4 | 0 | 180 | 35 |
| Example 8 | 550 | 70 | 40-45 |
| Example 9 | 550 | 35 | 65-70 |
| Example 10 | 550 | 0 | 155 |

The experiments show that, irrespective of the feed point, it is surprisingly possible that the amine-containing water of reaction from an amine-catalytic process can be disposed of in a thermal oxidizer with formation of only very small amounts of nitrogen oxide and with feeding-in of only small amounts or even no ammonia.

The comparison of Example 7 with Example 10 additionally shows that the feed point for the amine-containing aqueous solution into the thermal oxidizer has an additional surprising effect in relation to the reduction in nitrogen oxide formation. Example 7 additionally shows, very surprisingly, that it is possible, by virtue of the method according to the invention, to entirely dispense with the ammonia feed in the reductive zone of the thermal oxidizer.

LIST OF REFERENCE NUMERALS

FIG. 1: Thermal oxidizer operated in accordance with the invention
(1) first zone of the thermal oxidizer
(2) second, oxidative zone of the thermal oxidizer
(3) third, reductive zone of the thermal oxidizer
(4) flame
(5) air or oxygen feed
(6) fuel feed
(7) feed of the amine-containing water of reaction
(8) optional feed of at least one further liquid to be combusted or of at least one gas to be combusted
(9) optional feed of ammonia or of a second amine

The invention claimed is:
1. A method for disposing of amine-containing water of reaction, where the amine-containing water is obtained from an amine-catalyzed process in which propanal is reacted with formaldehyde to give methacrolein, the method comprising:
combusting the amine-containing water of reaction in a thermal oxidizer consisting of:
a first zone comprising a burner, a fuel supply and an air supply;
a second, oxidative zone; and
a third, reductive zone having an oxygen content less than 3% by volume,
wherein a transition between the first and second zone is at a point in the thermal oxidizer where a temperature in the thermal oxidizer falls below 1100° C., and
wherein a transition between the second and third zone is at a point in the thermal oxidizer where the oxygen content within the thermal oxidizer falls below 3% by volume,
wherein the amine-containing water of reaction is not sprayed into the second, oxidative zone of the thermal oxidizer, and
wherein the amine-containing water of reaction is sprayed into the third, reductive zone of the thermal oxidizer.

2. The method of claim 1, comprising conducting a Mannich reaction continuously in the presence of 0.1 to 20 mol % of an organic amine base and 0.1 to 20 mol % of an acid, based in each case on propanal, at a temperature of 100 to 300° C. and at a pressure of 5 to 100 bar.

3. The method of claim 1, wherein the amine-containing water of reaction is taken from the bottom of a distillation column and the rest of the bottoms is passed into a reaction space of a plant.

4. The method of claim 1, wherein the amine-containing water of reaction is a retentate from the bottoms of a distillation column which have been passed through a membrane separation stage.

5. The method of claim 1, wherein a temperature between 850 and 1100° C. and an oxygen content between 5 and 21% by volume are present in the oxidative zone of the thermal oxidizer.

6. The method of claim 1, wherein the amine-containing water of reaction is sprayed directly into a flame of the first zone.

7. The method of claim 1, wherein ammonia, urea or an amine is additionally metered into the third, reductive zone of the thermal oxidizer.

8. The method of claim 1, wherein at least one liquid to be combusted, comprising an organic constituent, from another process is additionally metered into the first or second zone of the thermal oxidizer.

9. The method of claim 8, wherein the other process is a process for converting methacrolein to methyl methacrylate or methacrylic acid.

10. The method of claim 8, wherein the other process is a process for preparing propionaldehyde proceeding from ethylene and synthesis gas, which gives rise to a liquid waste phase comprising by-products and high boilers that are combusted in the thermal oxidizer.

11. The method of claim 1, wherein at least one gaseous phase to be combusted, comprising an organic constituent and/or hydrogen, from another process is additionally metered into the first or second zone of the thermal oxidizer.

12. The method of claim 11, wherein the other process is a process for preparing formalin proceeding from methanol, which gives rise to a hydrogenous offgas which is combusted in the thermal oxidizer.

13. The method of claim 1, wherein no ammonia, no urea, and no amine is metered into the third, reductive zone of the thermal oxidizer.

14. A method for disposing of amine-containing water of reaction, where the amine-containing water is obtained from an amine-catalyzed process in which propanal is reacted with formaldehyde to give methacrolein, the method comprising:

combusting the amine-containing water of reaction in a thermal oxidizer consisting of:
- a first zone comprising a burner, a fuel supply and an air supply;
- a second, oxidative zone; and
- a third, reductive zone having an oxygen content less than 3% by volume,
- wherein a transition between the first and second zone is at a point in the thermal oxidizer where a temperature in the thermal oxidizer falls below 1100° C., and
- wherein a transition between the second and third zone is at a point in the thermal oxidizer where the oxygen content within the thermal oxidizer falls below 3% by volume, wherein the amine-containing water of reaction is sprayed into the second, oxidative zone of the thermal oxidizer, and wherein ammonia is metered into the third, reductive zone of the thermal oxidizer.

15. The method of claim 14, wherein a temperature between 850 and 1100° C. and an oxygen content between 5 and 21% by volume are present in the oxidative zone of the thermal oxidizer.

16. The method of claim 14, wherein the amine-containing water of reaction is additionally sprayed directly into a flame of the first zone.

* * * * *